(12) United States Patent
Chen

(10) Patent No.: US 9,028,420 B2
(45) Date of Patent: May 12, 2015

(54) ELECTRONIC DEVICE AND METHOD FOR MEASURING PULSE

(75) Inventor: Jun-Dah Chen, New Taipei (TW)

(73) Assignee: Hon Hai Precision Industry Co., Ltd., New Taipei (TW)

( * ) Notice: Subject to any disclaimer, the term of this patent is extended or adjusted under 35 U.S.C. 154(b) by 760 days.

(21) Appl. No.: 13/209,459

(22) Filed: Aug. 15, 2011

(65) Prior Publication Data

US 2012/0316450 A1    Dec. 13, 2012

(30) Foreign Application Priority Data

Jun. 9, 2011    (TW) .............................. 100120234 A

(51) Int. Cl.
*A61B 5/02* (2006.01)
*A61B 5/024* (2006.01)
*A61B 5/00* (2006.01)

(52) U.S. Cl.
CPC .............. *A61B 5/024* (2013.01); *A61B 5/02444* (2013.01); *A61B 2562/0247* (2013.01); *A61B 5/7257* (2013.01)

(58) Field of Classification Search
USPC ......... 600/481, 483, 484, 485, 500–504, 508, 600/509, 513, 527, 528
See application file for complete search history.

(56) References Cited

U.S. PATENT DOCUMENTS

| 4,052,979 | A | * | 10/1977 | Scherr et al. | .................. | 600/503 |
| 4,112,491 | A | * | 9/1978 | Bugay | ............................ | 600/502 |
| 5,795,301 | A | * | 8/1998 | Yasukawa et al. | ............ | 600/500 |
| 6,023,662 | A | * | 2/2000 | Hayakawa et al. | ............. | 702/75 |
| 7,988,638 | B2 | * | 8/2011 | Novac | ............................ | 600/500 |
| 2009/0209870 | A1 | * | 8/2009 | Tanabe | ......................... | 600/500 |

OTHER PUBLICATIONS

Kolokowsky, Touchscreens 101: Understanding Touchscreen Technology and Design, Cypress Perform, pp. 1-5, Jun. 2009.*

* cited by examiner

*Primary Examiner* — Jacqueline Cheng
*Assistant Examiner* — Puya Agahi
(74) *Attorney, Agent, or Firm* — Novak Druce Connolly Bove + Quigg LLP

(57) ABSTRACT

The present disclosure provides an electronic device and a method of measuring pulse adapted for the device. The electronic device includes a capacitive type touch control unit to sense the change of pulse and the capacitive type touch control unit includes a capacitor. The method includes steps: detecting a pulse of a user in real time and sampling the pulse every sample period, measuring charge-discharge time of the capacitor according to the sampled pulse at each sample period, counting a capacitance value of the capacitor according to the charge-discharge time corresponding to each sampled pulse, and forming a first wave form showing all counted capacitance values of the capacitor. Doing a spectrum analysis of the all counted capacitance values and performing a Fourier Transform to obtain a second wave form of pulse frequency-amplitude, and displaying the second wave form.

5 Claims, 3 Drawing Sheets

ELECTRONIC DEVICE AND METHOD FOR MEASURING PULSE

BACKGROUND

1. Technical Field

The disclosure relates to an electronic device and, more particularly, to an electronic device for measuring pulse and a method of measuring pulse adapted for the electronic device.

2. Description of Related Art

Heart rate is represented by the pulse rate of the body. This pulse rate can be measured on the wrist where the pulse can be sensed by applying to it. However, often when the pulse rate is measured, a belt composed of fibre material is wrapped and bound tight on a wrist of the user, which may be uncomfortable for the user.

Therefore, what is needed is an electronic device for measuring pulse to overcome the described shortcoming.

DETAILED DESCRIPTION

Figure 1:
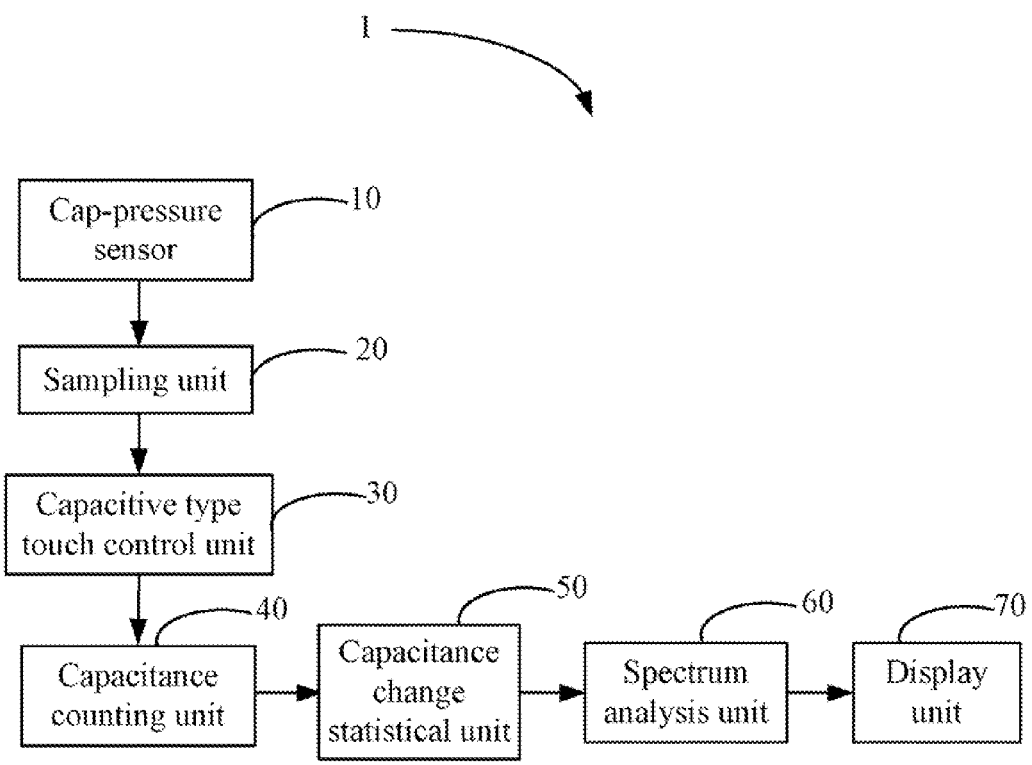
FIG. 1 is a block diagram of an electronic device for measuring pulse, in accordance with an exemplary embodiment.

FIG. 1 is a block diagram of an electronic device 1 for measuring pulse, in accordance with an exemplary embodiment. The electronic device 1 for measuring pulse (hereinafter "electronic device") includes a cap-pressure sensor 10, a sampling unit 20, a capacitive type touch control unit 30, a capacitance counting unit 40, a capacitance change statistical unit 50, a spectrum analysis unit 60, and a display unit 70. The display unit 40 is configured for displaying information.

The cap-pressure sensor 10 detects and senses a pulse of a user in real time. When a wrist of the user is close to the cap-pressure sensor 10, the cap-pressure sensor 10 can sense the pulse of the wrist. The sampling unit 20 samples the pulse every sample period. For example, the sample period is 0.01 second, and the sampling unit 20 samples the pulse P1 at 0.01 second and P2 at 0.02 second.

Figure 2:
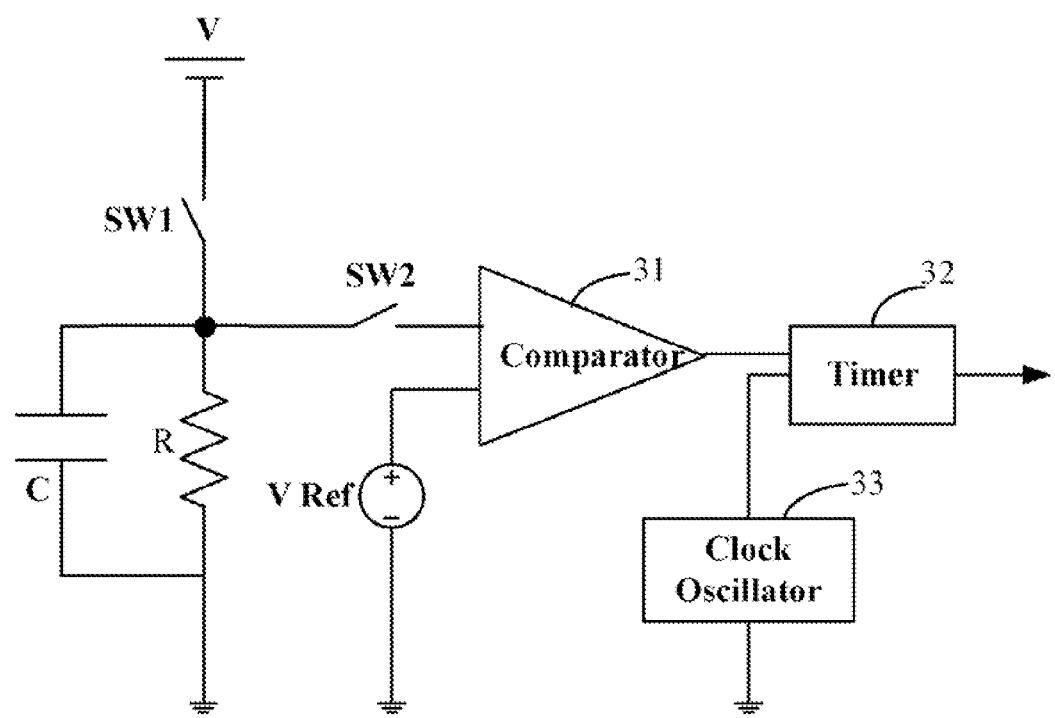
FIG. 2 is a circuit diagram of a capacitive type touch control unit of the electronic device of FIG. 1.

The capacitive type touch control unit 30 includes a capacitor and measures charge-discharge time of the capacitor according to the sampled pulse at each sample period. Once the sampled pulse changes, the charge-discharge time of the capacitor correspondingly changes. FIG. 2 is a circuit diagram of a capacitive type touch control unit 30 of FIG. 1. The capacitive type touch control unit 30 includes the capacitor C, a resistance R, two switches SW1, SW2, a comparator 31, a timer 32, and a clock oscillator 33. The first switch SW1 is connected to a power voltage V and the resistance R. The capacitor C and the resistance R are in parallel. One end of the switch SW2 is connected to a node between the switch SW1 and the resistance R and the other is connected to an input terminal of the comparator 31. A reference voltage VRef is connected to the input terminal of the comparator 31. The output terminal of the comparator 31 is connected to the input terminal of the timer 32 and the clock oscillator 33 is connected to the input terminal of the timer 32. The output terminal of the timer 32 is connected to the capacitance counting unit 40.

When the cap-pressure sensor 10 does not detect the pulse, the value of the capacitor C is constant and charge-discharge time of the capacitor C is constant. When the sampling unit 20 samples a changed pulse, the switch SW1 is off and the switch SW2 is on, and the timer 32 starts to measure time. The circuit charges the capacitor C for a predetermined time period and enters in a steady state.

When the measured time reaches the predetermined time period, the switch SW1 is on and the switch SW2 is off, the capacitor C and the resistance R form a RC loop. The circuit starts to discharge for the capacitor C and decreases the voltage of the resistance R. The comparator 31 acquires the reference voltage VRef and compares the reference voltage VRef with the voltage of the capacitor C. When the voltage of the capacitor C reaches the reference voltage VRef, the timer 32 stops timing and measures the charge-discharge time T of the capacitor C according to a clock signal generated from the clock oscillator 33.

The capacitance counting unit 40 counts a capacitance value of the capacitor C according to the charge-discharge time T corresponding to each sampled pulse and a formula $c=T/r$, wherein c represents the capacitance value of the capacitor C and r represents a value of the resistance R. The capacitance change statistical unit 50 forms a first wave form showing all counted capacitance values of the capacitor C in the sampled periods. For example, horizontal ordinate represents sample time, vertical ordinate represents the capacitance value of the capacitor in the first wave form, and each sample period corresponds to a capacitance value. Because the pulse of the user changes, which leads to the change of the capacitance value of the capacitor C, the first wave form reflects the change of the pulse. In the embodiment, the capacitance value of the capacitor C is direct ratio to the pulse of the user.

The spectrum analysis unit 60 does the spectrum analysis of the all counted capacitance values and performs a Fourier Transform on the analyzed spectrum to obtain a second wave form of pulse frequency-amplitude, and controls the display unit 70 to display the second wave form. Therefore, the peak value of the amplitude in the second wave form corresponds to the pulse rate of the user. In the embodiment, the capacitive type touch control unit 30 and the display unit 70 forms a capacitive type touch screen.

Figure 3:
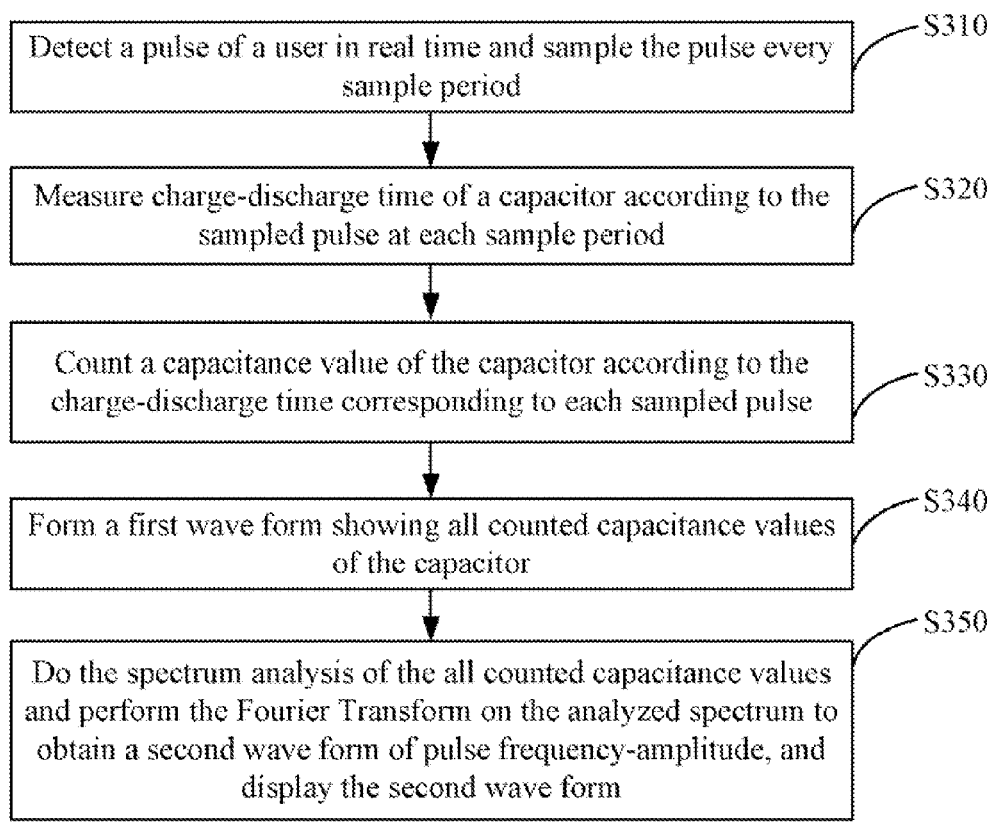
FIG. 3 is a flowchart of a method of measuring pulse adapted for the electronic device of FIG. 1.

FIG. 3 is a flowchart of a method of measuring pulse adapted for the electronic device of FIG. 1. The cap-pressure sensor 10 detects and senses the pulse for the user in real time and the sampling unit 20 samples the pulse every sample period in step S310. The capacitive type touch control unit 30 measures the charge-discharge time of the capacitor C according to the sampled pulse at each sample period in step S320. The capacitance counting unit 40 counts the capacitance value of the capacitor C according to the charge-discharge time T corresponding to each sampled pulse in step S330.

The capacitance change statistical unit 50 forms the first wave form showing all counted capacitance values of the capacitor in step S340. The spectrum analysis unit 60 does the spectrum analysis of the all counted capacitance values and performs the Fourier Transform on the analyzed spectrum to obtain the second wave form of pulse frequency-amplitude, and controls the display unit 70 to display the second wave form.

Therefore, the electronic device 1 adopts the capacitive type touch control circuit to count the change of the capacitance value of the capacitor C and the change of the capacitance value of the capacitor C reflects the changed of the pulse of the user. The user may learn about his/her pulse rate from the second wave form and no need to bind the wrist of the user to obtain the pulse rate.

Although the present disclosure has been specifically described on the basis of the exemplary embodiment thereof, the disclosure is not to be construed as being limited thereto. Various changes or modifications may be made to the embodiment without departing from the scope and spirit of the disclosure.

What is claimed is:

1. An electronic device for measuring a pulse rate of a user comprising: a display unit;
   a cap-pressure sensor to detect a pulse of a user in real time;
   a sampling unit to sample the pulse every sample period;
   a capacitive type touch control unit comprising a capacitor and to measure charge-discharge time of the capacitor according to the sampled pulse at each sample period;
   a capacitance counting unit to count a capacitance value of the capacitor according to the charge-discharge time corresponding to each sampled pulse;
   a capacitance change statistical unit to form a first wave form showing all counted capacitance values of the capacitor;
   a spectrum analysis unit to do a spectrum analysis of the all counted capacitance values to obtain an analyzed spectrum and perform a Fourier Transform on the analyzed spectrum to obtain a second wave form of pulse frequency-amplitude, and control the display unit to display the second wave form; and
   wherein a peak value of the amplitude in the second wave form corresponds to the pulse rate of the user.

2. The electronic device as recited in claim 1, wherein the capacitive type touch control unit further comprises a resistance, two switches (SW1, SW2), a timer, and a clock oscillator; a first switch (SW1) is connected to a power voltage and the resistance, the capacitor and the resistance are in parallel, one end of a second switch (SW2) is connected to a node between the first switch (SW1) and the resistance and the other is connected to an input terminal of the comparator, a reference voltage is connected to the input terminal of the comparator, the output terminal of the comparator is connected to the input terminal of the timer and the clock oscillator is further connected to the input terminal of the timer, and the output terminal of the timer is connected to the capacitance counting unit.

3. The electronic device as recited in claim 2, wherein when the cap-pressure sensor does not detect the pulse, the value of the capacitor is constant and charge-discharge time of the capacitor is constant, when the sampling unit samples a changed pulse, the first switch (SW1) is off and the second switch (SW2) is on, and the timer starts to measure time, when the circuit charges the capacitor for a predetermined time period, the first switch (SW1) is on and the second switch (SW2) is off, the capacitor and the resistance form a resistor-capacitor (RC) loop, the RC loop starts to discharge the capacitor and decreases the voltage of the resistance, and when the voltage of the capacitor reaches a reference voltage, the timer stops timing and measures the charge-discharge time of the capacitor.

4. The electronic device as recited in claim 3, wherein the capacitance counting unit counts the capacitance value of the capacitor according to the charge-discharge time corresponding to each sampled pulse and a formula $c=T/r$, wherein c represents the capacitance value of the capacitor, T represents the charge-discharge time of the capacitor, and r represents a value of the resistance.

5. A method of measuring a pulse rate of a user adapted for an electronic device, the electronic device comprising a capacitive type touch control unit to sense the change of pulse and the capacitive type touch control unit comprising a capacitor, the method comprising:
   detecting the pulse for the user in real time and sampling the pulse every sample period;
   measuring charge-discharge time of the capacitor according to the sampled pulse at each sample period;
   counting a capacitance value of the capacitor according to the charge-discharge time corresponding to each sampled pulse;
   forming a first wave form showing all counted capacitance values of the capacitor; doing a spectrum analysis of the all counted capacitance values to obtain an analyzed spectrum and performing a Fourier Transform on the analyzed spectrum to obtain a second wave form of pulse frequency-amplitude, and displaying the second wave form; and
   wherein a peak value of the amplitude in the second wave form corresponds to the pulse rate of the user.

* * * * *